United States Patent
Ryo et al.

(10) Patent No.: US 10,731,134 B2
(45) Date of Patent: Aug. 4, 2020

(54) PRODUCTION METHOD FOR ARTIFICIAL CANCER STEM CELL AND INDUCED DIFFERENTIATION METHOD THEREFOR

(75) Inventors: Akihide Ryo, Yokohama (JP); Mayuko Nishi, Yokohama (JP)

(73) Assignee: Public University Corporation Yokohama City University, Kanagawa (JP)

(*) Notice: Subject to any disclaimer, the term of this patent is extended or adjusted under 35 U.S.C. 154(b) by 122 days.

(21) Appl. No.: 14/122,634

(22) PCT Filed: May 24, 2012

(86) PCT No.: PCT/JP2012/063302
§ 371 (c)(1),
(2), (4) Date: Nov. 26, 2013

(87) PCT Pub. No.: WO2012/165287
PCT Pub. Date: Dec. 6, 2012

(65) Prior Publication Data
US 2014/0120571 A1    May 1, 2014

(30) Foreign Application Priority Data
May 27, 2011 (JP) ................... 2011-118557

(51) Int. Cl.
*C12N 5/00* (2006.01)
*C12N 5/095* (2010.01)
*G01N 33/50* (2006.01)

(52) U.S. Cl.
CPC ....... *C12N 5/0695* (2013.01); *G01N 33/5011* (2013.01); *G01N 33/5073* (2013.01); *C12N 2501/602* (2013.01); *C12N 2501/603* (2013.01); *C12N 2501/604* (2013.01); *C12N 2501/606* (2013.01); *C12N 2503/00* (2013.01); *C12N 2506/30* (2013.01); *C12N 2510/00* (2013.01)

(58) Field of Classification Search
CPC .......... G01N 33/5011; G01N 33/5073; C12N 5/0695
See application file for complete search history.

(56) References Cited

U.S. PATENT DOCUMENTS

| | | |
|---|---|---|
| 2010/0240090 A1 | 9/2010 | Sakurada et al. |
| 2011/0091869 A1 | 4/2011 | Sasai et al. |
| 2012/0142005 A1 | 6/2012 | Hosoya et al. |
| 2012/0156778 A1 | 6/2012 | Egusa et al. |
| 2013/0198876 A1 | 8/2013 | Ishikawa |

FOREIGN PATENT DOCUMENTS

| | | |
|---|---|---|
| JP | 2008-182912 A | 8/2008 |
| JP | 2008-307007 A | 12/2008 |
| WO | WO 2009/148170 A1 | 12/2009 |
| WO | WO 2010/134526 A1 | 11/2010 |
| WO | WO 2010/137722 A1 | 12/2010 |
| WO | WO 2011/016261 A1 | 2/2011 |
| WO | WO 2011/024550 A1 | 3/2011 |
| WO | WO 2011/049099 A1 | 4/2011 |
| WO | WO 2011/060100 A1 | 5/2011 |
| WO | WO 2011/062559 A1 | 5/2011 |
| WO | WO 2011/148983 A1 | 12/2011 |
| WO | WO 2012/057052 A1 | 5/2012 |

OTHER PUBLICATIONS

Takahashi et al (Cell, 131: 861-872, 2007).*
Cancer Research, 50: 6075-6086, 1990).*
Jasmin et al (Stem Cells and Development, 19(3): 403-411, 2000)a.*
Miki et al ([Cancer Res 2007; 67(7): 3153-61]).*
Cowell et al (Cancer Genetics and Cytogenetics, 163: 23-29, 2005).*
Debnath et al (Methods, 30: 256-268, 2003).*
Li et al (Nature, 460: 1136-1139, 2009).*
Yu et al (Oncogene, 30(18): 2161-2172, 2011).*
Ginestier et al (Cell Stem Cell, 1(5): 555-567, 2007).*
Visvader et al (Nature Reviews, 8: 755-768, 2008).*
(Beltran et al. Breast Cancer Research, 13:R94, 1-21, 2011.*
Soule et al (Cancer Research, 50: 6075-6086, 1990) (Year: 1990).*
Bendall (Nature, 448(30); 1015-1021, 2007) (Year: 2007).*
Dvorak (FEBS Letters, 580:2869-2874, 2006) (Year: 2006).*
Beltran et al., "Generation of tumor-initiating cells by exogenous delivery of OCT4 transcription factor," Breast Cancer Research (2011), 13:R94, pp. 1-21.
Extended European Search Report dated Nov. 20, 2014, in European Patent Application No. 12792225.0.
Gupta et al., "Identification of Selective Inhibitors of Cancer Stem Cells by High-Throughput Screening," Cell (Aug. 21, 2009), vol. 138, pp. 645-659.
Nagai et al., "Long-term culture following ES-like gene-induced reprogramming elicits an aggressive phenotype in mutated cholangiocellular carcinoma cells," Biochem. Biophys. Res. Comm. (2010), vol. 395, pp. 258-263.
Scaffidi, P. and T. Misteli, "In vitro generation of human cells with cancer stem cell properties," Nature Cell Biology (Sep. 2011), vol. 13, No. 9, pp. 1051-1063.

(Continued)

Primary Examiner — Anoop K Singh
Assistant Examiner — Magdalene K Sgagias
(74) Attorney, Agent, or Firm — Morgan, Lewis & Bockius LLP

(57) ABSTRACT

It is intended to provide a cancer stem cell and a method for preparing the same. The present invention provides a method for preparing a pluripotent cancer stem cell, comprising transferring Oct3/4, Sox2, Klf4, and c-Myc genes to an immortalized epithelial cell. The present invention also provides a pluripotent cancer stem cell as prepared by the above method.

9 Claims, 7 Drawing Sheets
Specification includes a Sequence Listing.

(56) References Cited

OTHER PUBLICATIONS

Utikal et al., "Immortalization eliminates a roadblock during cellular reprogramming into iPS cells," Nature (Aug. 27, 2009), vol. 460, pp. 1145-1149.
Zhang et al., "SOX4 Induces Epithelial-Mesenchymal Transition and Contributes to Breast Cancer Progression," Cancer Res. (Jul. 11, 2012), vol. 72, No. 17, pp. 4597-4608.
English translation of the International Preliminary Report on Patentability (Forms PCT/IB/338 and PCT/IPEA/409), dated Nov. 28, 2013, for International Application No. PCT/JP2012/063302.
Achanzer et al., "Cadmium-induced Malignant Transformation of Human Prostate Epithelial Cells", Cancer Research, Jan. 15, 2001, vol. 61, pp. 455-458.
Bello et al., "Androgen responsive adult human prostatic epithelial cell lines immortalized by human papillomavirus 18", Carcinogenesis, 1997, vol. 18., No. 6, pp. 1215-1223.
Boukamp et al., "Normal Keratinization in a Spontaneously Immortalized Aneuploid Human Keratinocyte Cell Line", The Journal of Cell Biology, Mar. 1988, vol. 106, pp. 761-771.
International Search Report for PCT/JP2012/063302 dated Aug. 21, 2012.
Miura et al., "Variation in the safety of induced pluripotent stem cell lines", Nature Biotechnology, 2009.08, vol. 27, No. 8, pp. 743-745.
Miyoshi et al., "Defined factors induce reprogramming of gastrointestinal cancer cells", Proceedings of the National Academy of Sciences USA, Jan. 5, 2010, vol. 107, No. 1, pp. 40-45.
Nakanishi, "iPS Saibo to Gan Kansaibo no Sogo Rikai, Mechanism of malignant transformation of iPS-derived cells", Regenerative Medicine, 2010, vol. 9, No. 2, pp. 216-221.
Schurer et al., "Lipid composition and synthesis of HaCaT cells, an immortalized human keratinocyte line, in comparison with normal human adult keratinocytes", Experimental Dermatology, 1993, vol. 2, pp. 179-185.
Takano et al., "Hito Fushika Nyusen Johi Saibo MCF-10A kara no iPS Saibo (induced pluripotent stem cells) Juritsu", The Japanese Society for Regenerative Medicine, 2009, vol. 8, P-129, p. 253.
Utikal et al., "Sox2 is dispensable for the reprogramming of melanocytes and melanoma cells into induced pluripotent stem cells", Journal of Cell Science, Oct. 1, 2009, vol. 122, No. 19, pp. 3502-3510.
Bisson et al., "WNT signaling regulates self-renewal and differentiation of prostate cancer cells with stem cell characteristics", Cell Research (2009), vol. 19, pp. 683-697.
Chen et al., "Highly enriched CD133+CD44+ stem-like cells with CD133+CD44high metastatic subset in HCT116 colon cancer cells", Clin Exp Metastasis (2011), vol. 28, pp. 751-763.
Kryczek et al., "Expression of aldehyde dehydrogenase and CD133 defines ovarian cancer stem cells", Int. J. Cancer (2011), pp. 1-11.
Office Action issued in EP 12792225.0 dated Dec. 10, 2018.
Zhu et al., "Cancer stem/progenitor cells are highly enriched in CD133+CD44+ population in hepatocellular carcinoma", Int. J. Cancer (2010), vol. 126, pp. 2067-2078.
Office Action issued in EP Application No. 12792225.0 dated Jun. 13, 2017.
Singh et al., "Identification of a Cancer Stem Cell in Human Brain Tumors", Cancer Research & 104th Annual Meeting of the American-Association-for-Cancer-Research (AACR), Washington DC, USA, Apr. 6-10, 2013, vol. 63, No. 18, Sep. 15, 2013, pp. 5821-5828, XP-002390120.

\* cited by examiner

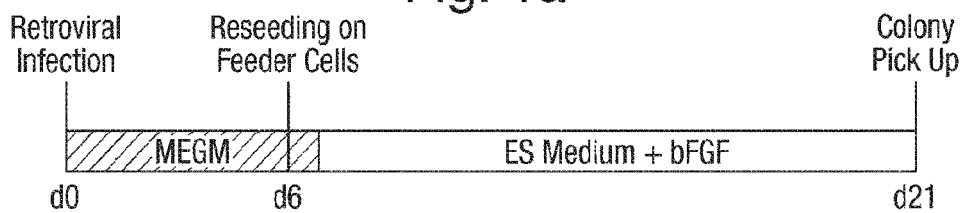
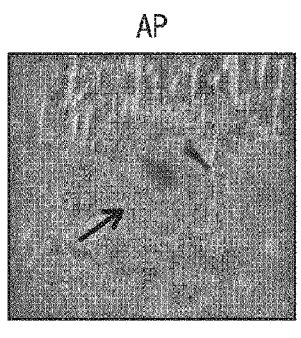
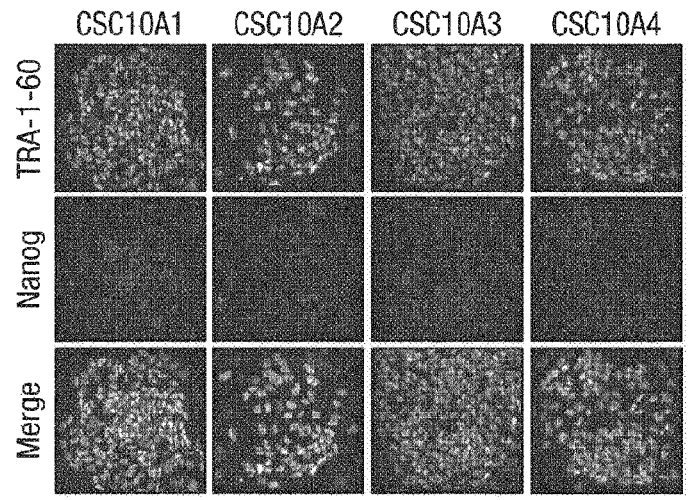
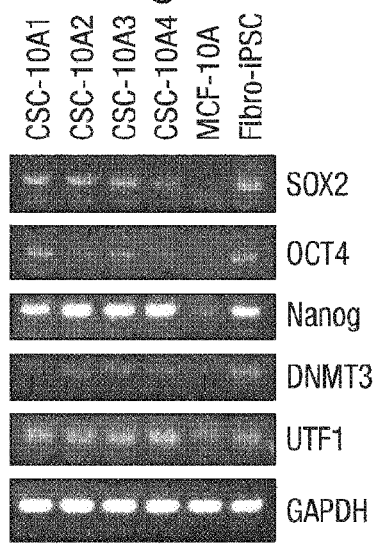
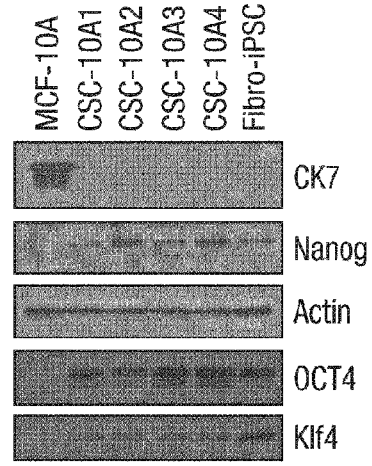

MCF-10A    CSC10A1

Fig. 3a
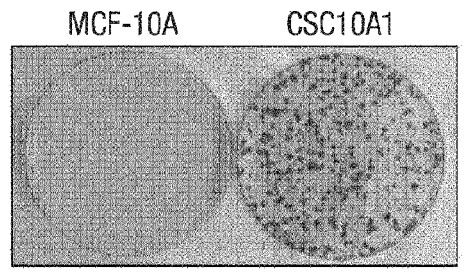
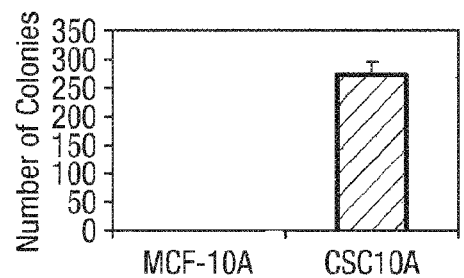
Fig. 3b
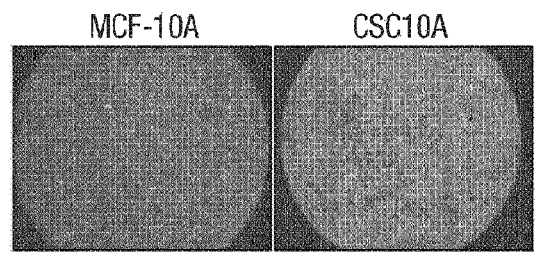
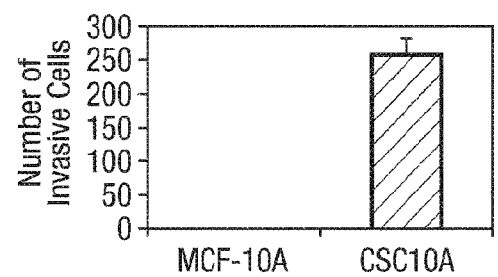
Fig. 3c
Soft Agar
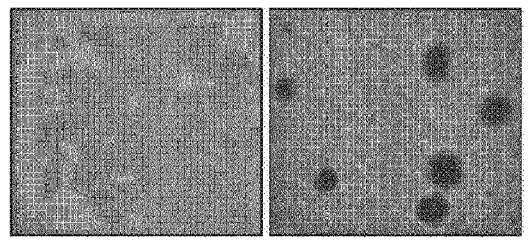
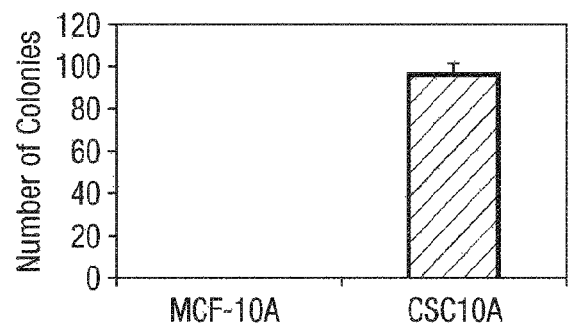

Fig. 6a
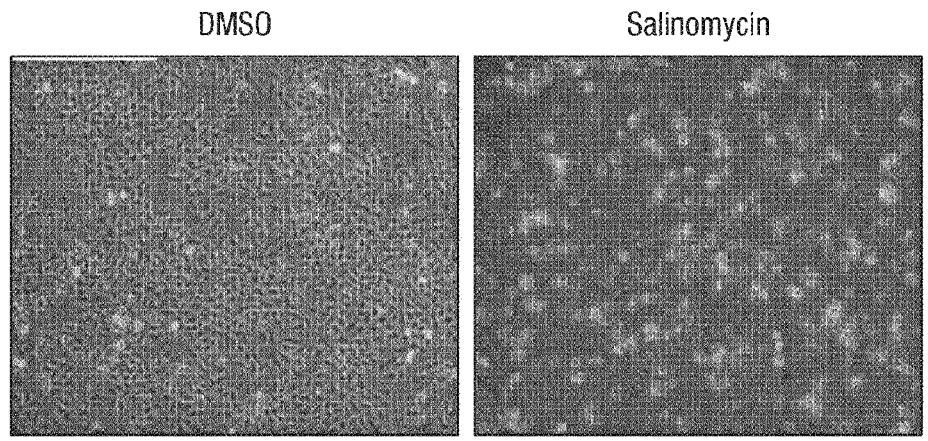
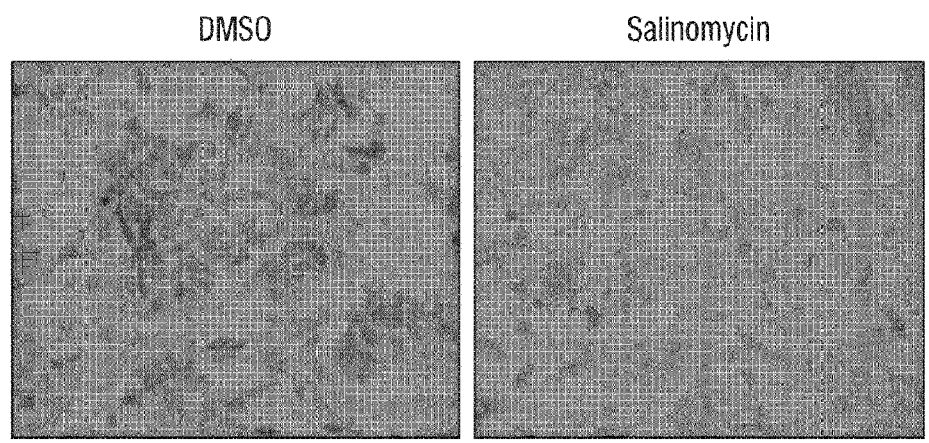
Fig. 6b
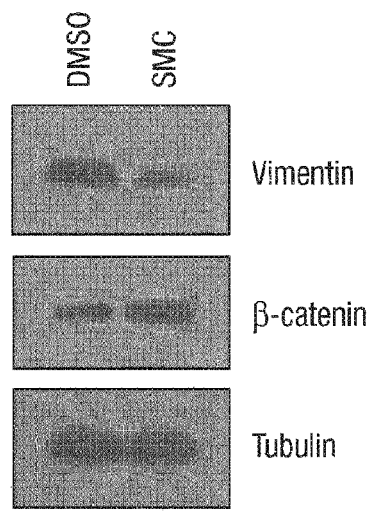

SEQUENCE LISTING

<160> NUMBER OF SEQ ID NOS: 14

<210> SEQ ID NO 1
<211> LENGTH: 492
<212> TYPE: DNA
<213> ORGANISM: Homo sapiens

<400> SEQUENCE: 1

```
atggcggacg aggagaagct gccgcccggc tgggagaagc gcatgagccg cagctcaggc    60
cgagtgtact acttcaacca catcactaac gccagccagt gggagcggcc cagcggcaac   120
agcagcagtg gtggcaaaaa cgggcagggg gagcctgcca gggtccgctg ctcgcacctg   180
ctggtgaagc acagccagtc acggcggccc tcgtcctggc ggcaggagaa gatcacccgg   240
accaaggagg aggccctgga gctgatcaac ggctacatcc agaagatcaa gtcgggagag   300
gaggactttg agtctctggc ctcacagttc agcgactgca gctcagccaa ggccagggga   360
gacctgggtg ccttcagcag aggtcagatg cagaagccat ttgaagacgc ctcgtttgcg   420
ctgcggacgg gggagatgag cgggcccgtg ttcacggatt ccggcatcca catcatcctc   480
cgcactgagt ag                                                      492
```

<210> SEQ ID NO 2
<211> LENGTH: 163
<212> TYPE: PRT
<213> ORGANISM: Homo sapiens

<400> SEQUENCE: 2

```
Met Ala Asp Glu Glu Lys Leu Pro Pro Gly Trp Glu Lys Arg Met Ser
1               5                   10                  15

Arg Ser Ser Gly Arg Val Tyr Tyr Phe Asn His Ile Thr Asn Ala Ser
            20                  25                  30

Gln Trp Glu Arg Pro Ser Gly Asn Ser Ser Gly Gly Lys Asn Gly
        35                  40                  45

Gln Gly Glu Pro Ala Arg Val Arg Cys Ser His Leu Leu Val Lys His
    50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
                100                 105                 110

Cys Ser Ala Lys Ala Arg Gly Asp Leu Gly Ala Phe Ser Arg Gly
            115                 120                 125

Gln Met Gln Lys Pro Phe Glu Asp Ala Ser Phe Ala Leu Arg Thr Gly
        130                 135                 140

Glu Met Ser Gly Pro Val Phe Thr Asp Ser Gly Ile His Ile Ile Leu
145                 150                 155                 160

Arg Thr Glu

<210> SEQ ID NO 3
<211> LENGTH: 26
<212> TYPE: DNA
<213> ORGANISM: Artificial
<220> FEATURE:
<223> OTHER INFORMATION: SOX2 forward PCR primer

<400> SEQUENCE: 3
gggaaatggg aggggtgcaa aagagg                                        26

<210> SEQ ID NO 4
<211> LENGTH: 26
<212> TYPE: DNA
<213> ORGANISM: Artificial
<220> FEATURE:
<223> OTHER INFORMATION: SOX2 reverse PCR primer

<400> SEQUENCE: 4
ttgcgtgagt gtggatggga ttggtg                                        26

<210> SEQ ID NO 5
<211> LENGTH: 24
<212> TYPE: DNA
<213> ORGANISM: Artificial
<220> FEATURE:
<223> OTHER INFORMATION: OCT4 forward PCR primer

<400> SEQUENCE: 5
gacaggggga ggggaggagc tagg                                          24

<210> SEQ ID NO 6
<211> LENGTH: 26
<212> TYPE: DNA
<213> ORGANISM: Artificial
<220> FEATURE:
<223> OTHER INFORMATION: OCT4 reverse PCR primer

<400> SEQUENCE: 6
cttccctcca accagttgcc ccaaac                                        26
```

<210> SEQ ID NO 7
<211> LENGTH: 25
<212> TYPE: DNA
<213> ORGANISM: Artificial
<220> FEATURE:
<223> OTHER INFORMATION: Nanog forward PCR primer

<400> SEQUENCE: 7
cagccctgat tcttccacca gtccc                               25

<210> SEQ ID NO 8
<211> LENGTH: 25
<212> TYPE: DNA
<213> ORGANISM: Artificial
<220> FEATURE:
<223> OTHER INFORMATION: Nanog reverse PCR primer

<400> SEQUENCE: 8
tggaaggttc ccagtcgggt tcacc                               25

<210> SEQ ID NO 9
<211> LENGTH: 25
<212> TYPE: DNA
<213> ORGANISM: Artificial
<220> FEATURE:
<223> OTHER INFORMATION: DNMT3 forward PCR primer

<400> SEQUENCE: 9
tgctgctcac agggcccgat acttc                               25

<210> SEQ ID NO 10
<211> LENGTH: 28
<212> TYPE: DNA
<213> ORGANISM: Artificial
<220> FEATURE:
<223> OTHER INFORMATION: DNMT3 reverse PCR primer

<400> SEQUENCE: 10
tcctttcgag ctcagtgcac cacaaaac                            28

<210> SEQ ID NO 11
<211> LENGTH: 24
<212> TYPE: DNA
<213> ORGANISM: Artificial
<220> FEATURE:
<223> OTHER INFORMATION: UTF1 forward PCR primer

<400> SEQUENCE: 11
ccgtcgctga acaccgccct gctg                                24

<210> SEQ ID NO 12
<211> LENGTH: 24
<212> TYPE: DNA
<213> ORGANISM: Artificial
<220> FEATURE:
<223> OTHER INFORMATION: UTF1 reverse PCR primer

<400> SEQUENCE: 12
cgcgctgccc agaatgaagc ccac                                24

<210> SEQ ID NO 13
<211> LENGTH: 20
<212> TYPE: DNA
<213> ORGANISM: Artificial
<220> FEATURE:

```
<223> OTHER INFORMATION: GAPDH forward PCR primer

<400> SEQUENCE: 13
gtggacctga cctgccgtct                                                    20

<210> SEQ ID NO 14
<211> LENGTH: 20
<212> TYPE: DNA
<213> ORGANISM: Artificial
<220> FEATURE:
<223> OTHER INFORMATION: GAPDH reverse PCR primer

<400> SEQUENCE: 14
ggaggagtgg gtgtcgctgt                                                    20
```

PRODUCTION METHOD FOR ARTIFICIAL CANCER STEM CELL AND INDUCED DIFFERENTIATION METHOD THEREFOR

TECHNICAL FIELD

The present invention relates to a production method for an artificial cancer stem cell and an induced differentiation method therefor.

BACKGROUND ART

In recent years, stem cell biology research has advanced, and strongly suggested the existence of cancer stem cells in solid tumors or hematological tumors. These cancer stem cells are found as small subsets, also called side populations (SPs), in solid tumors. This population, in order to maintain the tumor mass, gives rise to many cancer cells, while preserving cancer stem cells that retain their anaplastic abilities exclusively by self-renewal. The tumors may be depleted efficiently of such cancer stem cells by targeting regulatory factors specific for the cancer stem cells. The development of such therapeutic drugs can lead to the radical cure of cancers. Unfortunately, these critical regulatory factors are difficult to identify, even if cancer stem cells derived from the tumors of cancer patients are collected or if samples of cancer cell lines are collected. Due to the heterogeneity of their fractions, neither can cancer stem cell-specific factors be identified nor can their inhibitors be searched for. Hence, 100% pure cancer stem cells, if prepared, would contribute to a great progress in the above research.

The cancer stem cells are defined by (1) self-renewal, (2) pluripotency, and (3) the ability to initiate cancer of the same phenotypes as parental cancer phenotypes when transplanted to immunodeficient mice. For the sake of convenience, the term "cancer stem cells" is defined as cancer cells having the ability to self-renew (capable of dividing into malignant tumors and phenotypically diverse tumor cell populations). Many tumors are derived from single cells that have grown in vivo and have been transformed into cancer stem cells having tumor initiating abilities. The origin of the cancer stem cells, however, has not yet been elucidated.

The cancer stem cells can be identified on the basis of the expression of various cell surface markers and recovered from the tumor mass or cancer cell line using a cell sorter. The cancer stem cells collected in this way, however, are heterogenous populations. These cells, except only a small number of cells, do not possess the characteristics of pure cancer stem cells and thus, cannot be regarded as cancer stem cells in the strict sense of the term.

Some solid tumors contain specific subpopulations termed side populations (SPs), which have acquired the functional properties of cancer stem cells. These cells are able to initiate the entire tumor through self-renewal or differentiation. In the cell populations of solid tumors, cells having certain cell surface markers are known to possess the characters of cancer stem cells. For example, in brain tumor (glioblastoma), prostate cancer, and colon cancer, CD133+ cells have been shown to be cancer stem cells either by experiments on the heterotransplantation to immunodeficient mice of CD133+ cells and CD133− cells separated from these cancers, or in view of their capacity for in vitro self-renewal and growth or differentiation (Non Patent Literatures 1 to 3).

Also, in breast cancer, fractions with high expression of CD44 and low expression of CD24 (CD44(+)CD24(−/low)) have been shown to have the properties of cancer stem cells (Non Patent Literature 4).

Unfortunately, these methods which depend on cell surface markers for separating cancer stem cells are less likely to separate 100% cancer stem cells. In addition, the cells thus separated are very difficult to maintain or amplify. Against this backdrop, attempts have been made to artificially prepare cancer stem cells.

Miyoshi et al. have recently reported that the expression of reprogramming factors in various gastrointestinal cancer cells (cancer cell lines) successfully induced cancer stem cells (Non Patent Literature 5).

These cells, however, were already transformed (malignantly altered or cancerated) and acquired many gene mutations or chromosomal abnormalities. The cells therefore did not constitute homogeneous cell populations and thus seem to be unsuitable for drug screening or biomarker research. Thus, these cells are rarely defined as pure cancer stem cells.

In this connection, Yamanaka et al. have shown that induced pluripotent stem cells (iPS cells), which are similar to embryonic stem cells (ES cells), can be generated from human fibroblasts by the transfer of four genes Sox2, Oct4, Klf4, and c-Myc using retrovirus vectors (Non Patent Literature 6).

Nonetheless, these four genes have not yet been transferred to immortalized human cells. In addition, no previous report has shown that the transfer of these four genes causes not only the reprogramming of cells but also their canceration to thereby form human cancer stem cells.

CITATION LIST

Non-Patent Literature

Non-Patent Literature 1: CD133+ and CD133− Glioblastoma-Derived Cancer Stem Cells Show Differential Growth Characteristics and Molecular Profiles. Dagmar Beier, et al. Cancer Res 2007 67 (9): 4010-4015 (Discovery of cancer stem cells of brain tumor)

Non-Patent Literature 2: Identification of Putative Stem Cell Markers, CD133 and CXCR4, in hTERT-Immortalized Primary Nonmalignant and Malignant Tumor-Derived Human Prostate Epithelial Cell Lines and in Prostate Cancer Specimens. Jun Miki, et al. Cancer Res 2007 67: (7) 3153-3161 (Discovery of cancer stem cells of prostate cancer)

Non-Patent Literature 3: Identification and expansion of human colon-cancer-initiating cells. Lucia Ricci-Vitiani, et al. Nature 2007 4 Jan. Vol. 445, 111-115 (Discovery of cancer stem cells of colon cancer)

Non-Patent Literature 4: Prospective identification of tumorigenic breast cancer cells. Al-Hajj M, Wicha S M, Benito-Hernandez A, Morrison S J, Clarke M F. Proc Natl Acad Sci USA. 2003; 100: 3983-3988. (Discovery of cancer stem cells of breast cancer)

Non-Patent Literature 5: Defined factors induce reprogramming of gastrointestinal cancer cells. Miyoshi N, Ishii H, Nagai K, Hoshino H, Mimori K, Tanaka F, Nagano H, Sekimoto M, Doki Y, Mori M. Proc Natl Acad Sci USA. 2010 Jan. 5; 107 (1): 40-5. Epub 2009 Dec. 14.

Non-Patent Literature 6: Induction of pluripotent stem cells from adult human fibroblasts by defined factors. Takahashi K, Tanabe K, Ohnuki M, Narita M, Ichisaka T, Tomoda K, Yamanaka S. Cell. 2007 Nov. 30; 131 (5): 861-72.

SUMMARY OF INVENTION

Technical Problem

An object of the present invention is to provide a cancer stem cell and a method for preparing the same.

Solution to Problem

Cancer stem cells are found as small cell populations in tumors and influence tumor growth or recurrence. A construction of in vitro cancer stem cell systems could lead to the elucidation of the properties of the cancer stem cells or the development of novel treatment of the cancer stem cells. In the present study, the inventors have established induced cancer stem cells (iCSCs or CSCs) from immortalized human cells (human mammary epithelial cells MCF-10A, human prostatic epithelial cells RWPE-1, and human skin keratinocytes HaCaT) by the gene transfer of four reprogramming factors, Oct3/4, Sox2, Klf4, and c-Myc, via a recombinant retrovirus or Sendai virus vector. These iCSCs are morphologically similar to ES cells or iPS cells and can maintain their self-renewal and anaplastic abilities by forming niches and then colonies on feeder cells (mouse embryonic fibroblasts). The iCSCs are able to initiate tumors when transplanted to immunodeficient mouse models. Upon in vitro differentiation of iCSCs as mediated by embryoid bodies, CD44+/CD24low cancer stem cells appear. These cells can be further differentiated into epithelial cancer cells expressing an epithelial marker cytokeratin 7 or cytokeratin 8/18. These cells exhibit malignant phenotypes in transformation assay such as soft agar colony formation assay or Matrigel invasion assay. Use of the cancer stem cell model constructed by the present inventors may potentially lead to a future development of novel diagnostic or therapeutic methods targeting cancer stem cells. The present invention has been completed on the basis of these findings. The aspects of the present invention are as follows:

(1) A method for preparing a pluripotent cancer stem cell, comprising transferring Oct3/4, Sox2, Klf4, and c-Myc genes to an immortalized epithelial cell.

(2) A pluripotent cancer stem cell prepared by the method according to (1).

(3) A method for preparing a cancer stem cell, comprising differentiating the pluripotent cancer stem cell according to (2).

(4) A cancer stem cell prepared by the method according to (3).

(5) A method for preparing a cancer cell, comprising differentiating the cancer stem cell according to (4).

(6) A cancer cell prepared by the method according to (5).

(7) A method for screening for a substance having an anticancer effect, comprising using the cell according to (2), (4), or (6).

The cancer stem cell model of the present invention is an induced cancer stem cell model developed by the present inventors before the rest of the world and can give rise to "cancer cells" at varying stages of differentiation ranging from undifferentiated cancer stem cells to differentiated cancer cells. Conventional cancer stem cells collected from patients' specimens are difficult to replicate, with their anaplastic abilities maintained. In addition, these conventional cells are differentiated in vitro with disadvantageously low efficiency. Use of the cancer stem cell model system of the present invention enables highly efficient and stable maintenance and replication of cancer stem cells. This system also enables large-scale culture of stem cells in a stable and easy manner while maintaining their undifferentiated state and will therefore make a great contribution to drug screening or biomarker search by targeting cancer stem cells.

The induced cancer stem cells as an original development by the present inventors were artificially generated from immortalized cells, unlike the conventional cancer stem cell lines composed of heterogeneous cell populations as separated from cancer cell lines. The cancer stem cells of the present invention therefore have a minimum accumulation of gene mutations or chromosomal abnormalities and can yield substantially 100% pure and stable homogeneous cancer stem cell populations. Use of these cells enables, for example, search for unknown cancer stem cell markers or screening for a compound that specifically kill cancer stem cells. This may potentially lead to the development of a novel molecular targeting therapy that targets cancer stem cells. Also, the cancer stem cell model of the present invention can be exploited as an important tool for enhancing the efficiency of drug discovery.

When compared with the present invention, the following can be remarked about the method for inducing cancer stem cells by the reprogramming of cancer cells (Non-Patent Literature 5):

1) In Non-Patent Literature 5, already transformed (malignantly altered) cells (cancer cells) were reprogrammed. The present study is novel in that cancer stem cells can be prepared from nearly normal immortalized human epithelial cells having no tumor initiating ability. This is unpredictable from the previously established facts.

2) Cancer cell lines contain cancer stem cells, albeit in small amounts, having tumor initiating abilities. The method for preparing cancer cells by the introduction of Yamanaka's four factors to cancer cells could have simply increased such cancer stem cells.

3) Cancer cells have high chromosomal instability and therefore involve a large accumulation of gene mutations or chromosomal abnormalities. In this respect, individual cancer cells largely vary in their genes. If cancer stem cells are obtained from such cell populations, it is difficult to separate with high reproducibility those cancer stem cells which have the same characters. Theoretically, the cancer stem cells prepared from cancer cell lines are rarely applicable to drug screening, etc.

4) Non-Patent Literature 5 states that cancer stem cells expressing ES or iPS markers can be prepared by the introduction of Yamanaka's four factors to cancer cell lines. Cancer stem cells found in vivo differ in the level of differentiation from pluripotent stem cells such as ES cells and iPS cells. The cells expressing ES or iPS markers must therefore be differentiated to some extent in order to obtain cells having properties equivalent to those of actual cancer stem cells. Nonetheless, Non-Patent Literature 5 makes no mention about this fact. The present invention also provides a method for inducing the differentiation of ES or iPS cells into usual cancer stem cells.

Advantageous Effects of Invention

The separation of cancer stem cells from human cancer tissues involves many difficulties such as their scarcity, complicated collection, and ethical issues. Use of the cells established by the present inventors enables appropriate preparation of cancer stem cells at various stages of differentiation in necessary amounts and can also promote the development of novel drugs targeting cancer stem cells and niches. These cells can also be used in, for example, the identification of novel cancer stem cell markers or the analysis of a molecular mechanism underlying the resistance of cancer stem cells to anticancer agents.

The present specification encompasses the contents described in the specification and/or drawings of Japanese Patent Application No. 2011-118557 on which the priority of the present application is based.

BRIEF DESCRIPTION OF DRAWINGS

FIG. 1 shows the preparation of induced cancer stem cells using immortalized human mammary epithelial cells. FIG. 1a shows a strategy for establishing undifferentiated cells by the expression of four reprogramming factors in MCF-10A. FIG. 1b shows that alkaline phosphatase staining-positive colonies were picked up. FIG. 1c shows that 4 clones of established CSC-10A were immunostained with undifferentiation markers. FIG. 1d shows that the expression of undifferentiation markers was confirmed for 4 CSC-10A clones as well as MCF-10A and 4F-iPS by RT-PCR. FIG. 1e shows that the expression of undifferentiation markers or differentiation markers was confirmed for 4 CSC-10A clones as well as MCF-10A and 4F-iPS by Western blot.

FIG. 2 shows the establishment of CSC-10A and CSC-10A-D9 that was induced by differentiation from CSC-10A. FIG. 2c: tumors shown in cross section; and FIGS. 2d and 2e: tumors as stained with HE).

FIG. 3 shows a study on the malignant phenotypes of induced cancer stem cells. FIG. 3a shows that CSC-10A-D9 and MCF-10A were subjected to focus formation assay. FIG. 3b shows that CSC-10A-D9 and MCF-10A were subjected to invasion assay. FIG. 3c shows that CSC-10A-D9 and MCF-10A were subjected to colony formation assay.

FIG. 4 shows the induction of cancer stem cells from immortalized human prostatic epithelial cells and immortalized human skin keratinocytes.

FIG. 6 shows that CSC-10A-D9 induced by differentiation from CSC-10A was treated with 10 μM salinomycin or DMSO, and the cells were morphologically observed 4 days later under a phase-contrast microscope (upper images in FIG. 6a). Upon salinomycin treatment, the cells differentiated into epithelial-like cells and the size of each individual cell increased. Also, these cells were stained with an undifferentiation marker alkaline phosphatase (ALP). As a result, the salinomycin treatment was found to cause a significant decrease in ALP-positive cells (lower images in FIG. 6). Next, these cells were lysed and subjected to Western blot. As a result, the salinomycin-treated cells exhibited a decrease in the expression of a stem cell (mesenchymal) marker vimentin and an increase in the expression of a differentiation (epithelial) marker beta-catenin (FIG. 6b).

DESCRIPTION OF EMBODIMENTS

Figure 2A:
FIG. 2a shows that CSC-10A or MCF-10A was mixed with an equal amount of Matrigel and subcutaneously injected to each SCID mouse.

Hereinafter, the present invention will be described in detail.

The present invention provides a method for preparing a pluripotent cancer stem cell, comprising transferring Oct3/4, Sox2, Klf4, and c-Myc genes to an immortalized epithelial cell.

In the method of the present invention, the immortalized epithelial cell to which Oct3/4, Sox2, Klf4, and c-Myc genes are to be transferred can be any immortalized non-cancer epithelial cell. Examples of the immortalized epithelial cell can include human mammary epithelial cells MCF-10A (ATCC Number: 10ACRL-10317 (TM), Designations: MCF), human prostatic epithelial cells RWPE-1 (purchased from ATCC; No. CRL-11609), and human skin keratinocytes HaCaT (Boukamp P, Petrussevska R T, Breitkreutz D, Hornung J, Markham A, Fusenig N E (1988) Normal keratinization in a spontaneously immortalized aneuploid human keratinocyte cell line. J Cell Biol 106: 761-771). Also, the immortalized epithelial cell may be any of primary cultured cells, subcultured cells, and established cell lines.

In order to transfer the Oct3/4, Sox2, Klf4 and c-Myc genes (reprogramming factors) to the immortalized epithelial cell to thereby prepare a pluripotent cancer stem cell, a reprogramming method based on the transduction of somatic cells with transcription factors (Oct3/4, Sox2, Klf4, and c-Myc) (Cell, 126, pp. 663-676, 2006; Cell, 131, pp. 861-872, 2007; Science, 318, pp. 1917-1920, 2007; Nature, 451, pp. 141-147, 2008; and "How to establish human iPS cells" Ver. 1 Kyoto University Institute for Integrated Cell-Material Sciences (iCeMS), Center for iPS Cell Research and Application, CiRA M & M, Jul. 4, 2008) is preferably used, though the method of the present invention is not limited to this method. Alternatively, a direct reprogramming method may be used (Nat. Cell Biol. 2011 March; 13 (3): 215-22; Cell 142, 375-386 (2010); Nature 463, 1035-1041 (2010); and PNAS 108 (19), 7838-7843 (2011)).

In the method of the present invention, peptidylprolyl isomerase Pin1 may be coexpressed with the factors necessary for the reprogramming of somatic cells (reprogramming factors). Specifically, the immortalized epithelial cell may be transduced with Pin1 simultaneously with or before or after the transduction with the factors necessary for the reprogramming of somatic cells. Alternatively, Pin1 protein may be introduced to the immortalized epithelial cell simultaneously with or before or after the transduction with the factors necessary for the reprogramming of somatic cells. The additional introduction of Pin1 can promote the formation of cancer stem cells.

The peptidylprolyl isomerase Pin1 is a new type of regulator that binds to a phosphorylated Ser/Thr-Pro motif and causes cis/trans isomerization of the protein structure via the peptide bond, thereby regulating the functions of the phosphorylated protein. This novel "post-phosphorylation" regulation mechanism is known to alter the activity, protein-protein bond, intracellular localization, and stability, etc. of the target protein and play an important role in expressing the functions of the phosphorylated protein. The structural change caused by the binding of Pin1 to the phosphorylated protein switches on or off other posttranslational modifications such as ubiquitination or SUMO modification. Pin1 has been shown to play a critical role in the pathogenesis of intractable diseases such as cancer, immunological disease, and neurodegenerative disease. Pin1 targets a wide range of phosphorylated proteins, which differ depending on the types of cells or tissues. Even in the same cell or tissue, its repertoire largely varies between normal and diseased conditions on account of the difference in the phosphorylated state of the substrate. The present inventors have found that Pin1 which employs Oct4 as a substrate in pluripotent stem cells regulates the maintenance of self-renewal or pluripotency of stem cells.

In order to coexpress Pin1 with the factors necessary for the reprogramming of somatic cells, DNAs encoding the factors necessary for the reprogramming of somatic cells may, for example, be incorporated into vectors that permit the expression of the DNAs and transferred to immortalized epithelial cells. Simultaneously with or before or after this procedure, a Pin1-encoding DNA may be incorporated into vectors that permit the expression of the DNA and transferred to the immortalized epithelial cells. The DNAs encoding the factors necessary for the reprogramming of somatic cells may all be incorporated into one vector, which in turn is transferred to immortalized epithelial cells, or the DNAs may respectively be incorporated into separate vectors, which in turn are transferred to immortalized epithelial cells. Also, the Pin1-encoding DNA may be incorporated into the vectors that already incorporate the DNAs encoding the factors necessary for the reprogramming of somatic cells, and the vectors are then transferred to the immortalized epithelial cells. Alternatively, the Pin1-encoding DNA may be incorporated into vectors different from the vectors that already incorporate the DNAs encoding the factors necessary for the reprogramming of somatic cells, and the vectors are then transferred to the immortalized epithelial cells. Examples of the vectors that permit the expression of the DNAs encoding the factors necessary for the reprogramming of somatic cells and the vectors that permit the expression of the Pin1-encoding DNA can include viral vectors, plasmids, and artificial chromosomes. These vectors are preferably viral vectors (e.g., retrovirus vectors, lentivirus vectors, adenovirus vector, adeno-associated virus vectors, or Sendai virus vectors), more preferably retrovirus vectors. For example, pMXs, pBabe, or pRetro retrovirus vectors can be used as the retrovirus vectors. Each vector may contain gene expression control sequences (a promoter, an enhancer, a transcription terminator, a start codon, a splicing signal, a polyadenylation site, a stop codon, etc.) and elements such as a cloning site, a drug resistance gene, and a reporter gene.

Information on the DNA sequence and amino acid sequence of Pin1 is obtained from the database GenBank under Accession Nos. human Pin1 NM006221, mouse Pin1 NMO23371, and rat Pin1 NM00110670. The DNA sequence and amino acid sequence of human Pin1 are shown in SEQ ID NOs: 1 and 2, respectively. Pin1 may be any of wild type and variants as long as the object of the present invention can be attained.

The immortalized epithelial cells can be transduced with the factors necessary for the reprogramming of somatic cells and Pin1 using an approach known in the art such as microinjection, liposomes, lipofection, electroporation, calcium phosphate method, or viral infection. Preferably, the immortalized epithelial cells thus transduced with the factors necessary for the reprogramming of somatic cells and Pin1 are recovered, then reseeded over feeder cells, and cultured. For example, mouse fibroblasts, SNL76/7, or human mesenchymal cells can be used as the feeder cells.

In the case of using immortalized epithelial cells other than from rodents (e.g., immortalized human epithelial cells), lentivirus encoding an ecotropic receptor capable of infecting only rodents may be used in order to enhance the efficiency of gene transfer and the safety of experimenters. In such a case, the ecotropic receptor capable of infecting only rodents may preferably be introduced to the target cells (e.g., immortalized human epithelial cells), with the factors necessary for the reprogramming of somatic cells and Pin1 being then introduced to the cells using an ecotropic retrovirus. Alternatively, packaging cells such as PLAT-E cells (designed to express an ecotropic virus-derived envelope glycoprotein (env)) may be transfected with retrovirus vectors to thereby enhance the efficiency of the viral infection of the target cells.

Preferably, the Pin1 protein is introduced to the immortalized epithelial cells simultaneously with or before or after the transduction with the factors necessary for the reprogramming of somatic cells by use of a method which involves adding a cell-penetrating signal to the protein, a method using a lipofection reagent, electroporation, the direct introduction of the Pin1 protein, the activation of the Pin1 protein, the induced expression of Pin1, or the like. The Pin1 protein may be activated by treating the immortalized epithelial cells with a protein kinase C inhibitor or a protein kinase A inhibitor. Examples of the protein kinase C inhibitor can include calphostin C, polymyxin B, rottlerin, Y-27632, PD 173074, and GF 109203X. Examples of the protein kinase A inhibitor can include staurosporine, SP600125, apigenin, LY 294002, KT5823, and KT5720. The Pin1 expression may be induced by the administration of a cell growth factor. Examples of the cell growth factor can include epidermal growth factors, fibroblast growth factors, and vascular endothelial growth factors. Alternatively, the Pin1 expression may be induced by the expression of a transcription factor E2F.

The pluripotent cancer stem cells thus induced (hereinafter, also referred to as "induced pluripotent cancer stem cells") are able to initiate tumors when transplanted to immunodeficient mouse models. Upon in vitro differentiation as mediated by embryoid bodies, CD44+/CD24low cancer stem cells can appear. These cells can be further differentiated into epithelial cancer cells that express an epithelial marker cytokeratin 7 or cytokeratin 8/18. These cells can exhibit malignant phenotypes in transformation assay such as soft agar colony formation assay or Matrigel invasion assay. Thus, the present invention also provides a pluripotent cancer stem cell as prepared by the above method.

The pluripotent cancer stem cell of the present invention is capable of expressing pluripotent stem cell markers (e.g., TAR-1-60 and Nanog). The pluripotent cancer stem cell of the present invention is also capable of expressing stem cell markers (e.g., Oct4 and Nanog).

The pluripotent cancer stem cell can be cultured, subcultured, and frozen by the application of methods for use in ES cells.

The present invention also provides a method for preparing a cancer stem cell, comprising differentiating the above pluripotent cancer stem cell, and a cancer stem cell as prepared by this method (hereinafter, also referred to as an "induced cancer stem cell"). The cancer stem cell of the present invention is capable of expressing epithelial cancer stem cell markers (e.g., CD44, CD133, and ABCG2).

The present invention further provides a method for preparing a cancer cell, comprising differentiating the above cancer stem cell, and a cancer cell as prepared by this method. The cancer cell of the present invention is capable of expressing epithelial differentiation markers (e.g., CK7 and CK8/18).

Figure 2B:
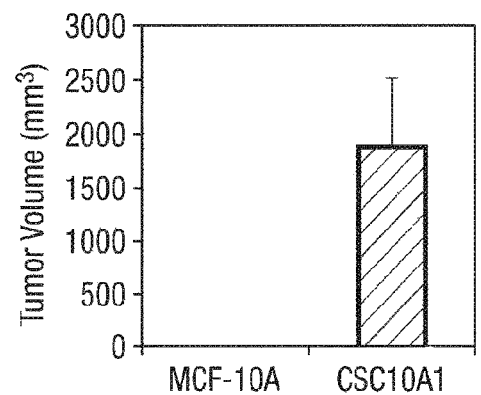
FIGS. 2b, 2c, 2d, and 2e show tumors that formed 9 weeks later (FIG. 2b: tumor size shown graphically.
Figure 2C:
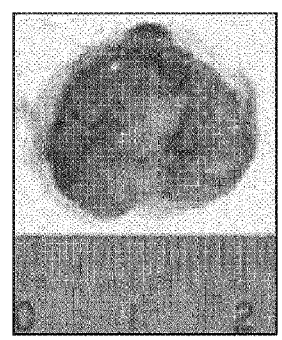
Figure 2D:
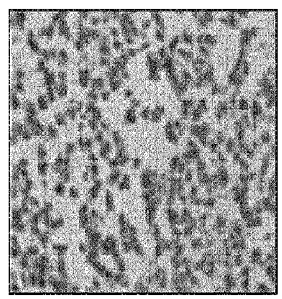
Figure 2E:
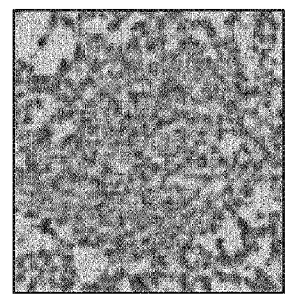
Figure 2F:
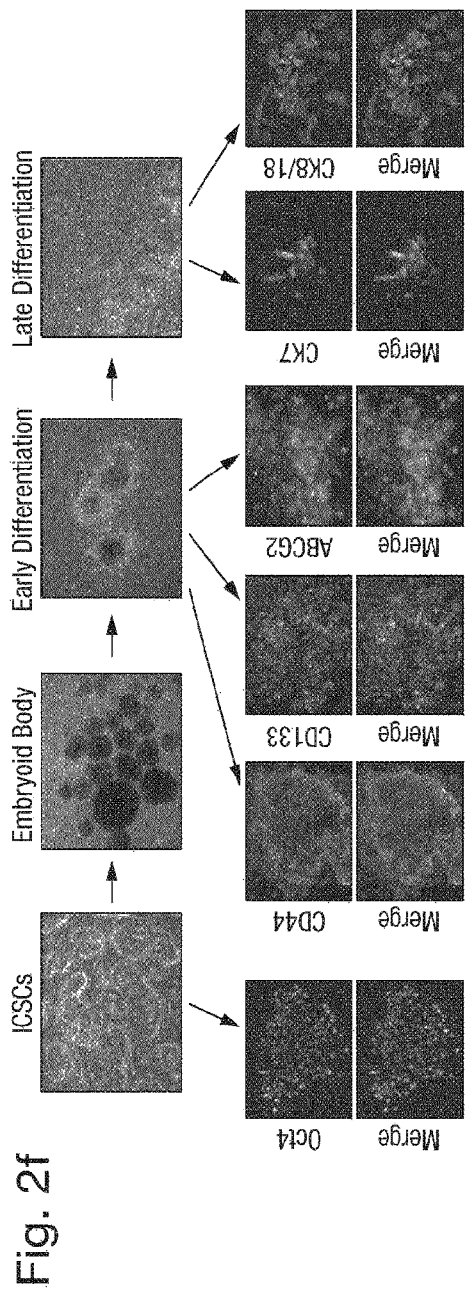
FIG. 2f shows that CSC-10A was immunostained in the course of induced differentiation using undifferentiation markers (Oct4), cancer stem cell markers (CD44, CD133, and ABCG2), and differentiated epithelial cell markers (CK7 and CK8/18).

Experiments described later in Examples have revealed the following: induced pluripotent cancer stem cells (iCSCs or iCSCs) form embryoid bodies when cultured for 7 days in a suspension culture system. At this stage, the induced pluripotent cancer stem cells are considered to have already differentiated into induced cancer stem cells. The embryoid bodies are cultured for 2 days in an adhesion system, whereupon the cells spread as a single layer that adheres to the bottom of the dish. This state is early differentiation (FIG. 2f). Further culture for 7 to 9 days results in late differentiation (FIG. 2f). At the stage of early differentiation, almost all of the cells are cancer stem cells which express cancer stem cell markers such as CD44 (CK7- or CK8/18-positive cells are absent at this stage). At the stage of late differentiation, some cells are differentiated, resulting in occasional emergence of foci of CK7- or CK8/18-positive cancer cells (CK7 and CK8/18 refer to markers of differentiated cancer cells (epithelial cells)). Yet 95% or more of all the cancer stem cells still remain undifferentiated in the late differentiation phase (i.e., only 5% or less of the cancer stem cells have been differentiated). The cells in the state of late differentiation (in the adhesion system) form embryoid bodies again after being brought back to the suspension system. Then, only induced cancer stem cells proliferate. The cells can again be brought back to the adhesion system to restore the state of early differentiation. Use of this approach can constantly yield fresh cancer stem cells. The induced cancer stem cells proliferate at such a fast rate that they are preferably subcultured every 3 days in 10-fold dilutions. Cancer stem cells and cancer cells can be prepared by the operation shown herein or a modification thereof.

Reportedly, the administration of salinomycin kills only cancer stem cells while leaving cancer cells intact (Gupta P B, Onder T T, Jiang G, Tao K, Kuperwasser C, Weinberg R A, Lander E S. Identification of selective inhibitors of cancer stem cells by high-throughput screening. Cell. 2009 Aug. 21; 138 (4): 645-59. Epub 2009 Aug. 13. PubMed PMID: 19682730.). This paper defines (CD44high/CD24low) cells as cancer stem cells and (CD44low/CD24high) cells as cancer cells according to analysis using a flow cytometer. This paper shows a blot from a flow cytometer on the right side of FIG. 4a, demonstrating that only (CD44low/CD24high) cancer cells were left intact upon addition of salinomycin to a population containing both cancer stem cells and cancer cells. To the contrary, only (CD44high/CD24low) cancer stem cells are left intact upon treatment with an anticancer agent Taxol (Tax). This indicates that salinomycin only inhibits the growth of cancer stem cells whereas Taxol only inhibits the growth of cancer cells (i.e., the cancer stem cells are not responsive but are resistant to Taxol). It can be expected that when the cells of the present invention are treated with salinomycin at the stage of late differentiation where cancer stem cells and cancer cells coexist, only the already existing cancer cells as shown above will increase. To the contrary, if the cells of the present invention are treated with Taxol (Tax), it can be expected that only cancer stem cells are left intact and can grow subsequently. In Examples described later, induced cancer stem cells (CSC-10A) treated with salinomycin exhibited a decrease in the expression of an undifferentiation marker alkaline phosphatase or a stem cell (mesenchymal) marker vimentin and an increase in the expression of a differentiation (epithelial) marker beta-catenin.

The present invention further provides a method for screening for a substance having an anticancer effect, by using the above pluripotent cancer stem cell, cancer stem cell, or cancer cell.

The screening method of the present invention involves, for example, culturing the pluripotent cancer stem cells, the cancer stem cells, or the cancer cells in the presence or absence of a test substance, followed by determination of the rate of cell survival. The test substance can be determined to have an anticancer effect if the cells cultured in the presence of the test substance exhibit a lower rate of survival than the cells cultured in the absence of the test substance.

The test substance may be of any kind. Examples of the test substance can include proteins, peptides, polysaccharides, oligosaccharides, monosaccharides, lipids, low-molecular-weight compounds, and nucleic acids (DNAs, RNAs, oligonucleotides, mononucleotides, etc.). These substances may be natural products or may be synthesized chemically or biochemically. Alternatively, substances produced by genetic engineering may be used.

EXAMPLES

Hereinafter, the present invention will be described specifically with reference to Examples. However, the present invention is not intended to be limited by these Examples.

Example 1

Results

Preparation of Induced Cancer Stem Cell Using Immortalized Human Cell

An outline of the preparation method and its time course is shown in FIG. 1a. Four genes Sox2, Oct3/4, Klf4, and c-Myc were transferred to cells of immortalized human mammary epithelial cell line MCF-10A (Pauley R J, Jones R F, Brooks S C. Isolation and characterization of a spontaneously immortalized human breast epithelial cell line, MCF-10.; Soule H D, Maloney T M, Wolman S R, Peterson W D Jr, Brenz R, McGrath C M, Russo J, Cancer Res. 1990 Sep. 15; 50 (18): 6075-86. (Establishment of MCF-10A cells)) using retrovirus vectors. Then, the cells were cultured in an MEGM medium for 6 days, then detached from the medium with trypsin-EDTA, and seeded over feeder cells (mouse fibroblasts). On the next day, the medium was replaced with a human ES medium, and the culture was continued with the medium replaced every two days. After 21 days, the cells were stained with alkaline phosphatase. Dark-red ES cell-like colonies were recovered one by one using a capillary (FIG. 1b). These cell groups were continuously cultured as cell clones in 24-well plates.

Of these, four typical clones were immunostained with pluripotent stem cell markers TAR-1-60 and Nanog; all of the four clones were confirmed to have expressed those markers (FIG. 1c).

These clones were also confirmed to have expressed a plurality of stem cell markers in analysis using RT-PCR (FIG. 1d) and Western blot (FIG. 1e).

These cells were subcutaneously injected, together with Matrigel, into each SCID mouse. As a result, the cancer stem cell-transplanted mouse developed tumors (FIGS. 2a, 2b, and 2c). Histological analysis showed that these tumors were composed of small undifferentiated cells, with no teratoma formation observed (FIGS. 2d and 2e). These results demonstrated that the prepared cell line was morphologically similar to iPS cells, but differed in properties from iPS cells.

Figure 2G:
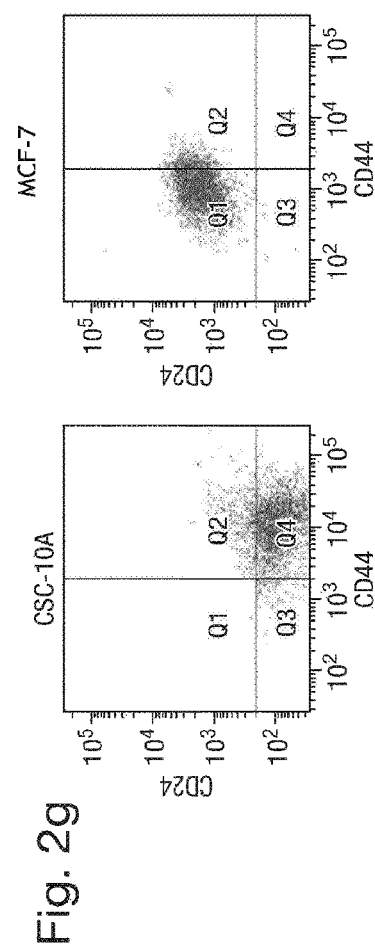
FIG. 2g shows that CSC-10A and MCF-7 cells stained with anti-CD44 and anti-CD24 antibodies were fractionated using a flow cytometer.

Next, these cells were cultured in surface-uncoated plates. After being cultured as spheres, the cells were attached to adhesion-system plates, whereupon spindle-shaped mesenchymal-like cells grew on the plates (FIG. 2f). The expression of conventional cancer stem cell markers CD44, CD133, and ABCG2 was confirmed for these cell groups by immunostaining. As a result, the expression of these markers was observed in all the clones (FIG. 2f). As a result of assaying marker molecules on the cell membranes using a flow cytometer, these cells were observed in CD44+/CD24low fractions, as in the case of conventional epithelial cancer stem cells (FIG. 2g). Next, these cells were subjected to a further long-term culture, whereupon a small number of cell groups differentiated spontaneously to form colonies that expressed a differentiated epithelial cell marker CK7 or CK8/18 (FIG. 2f). These results demonstrated that the cell line of interest can give rise to cells at varying stages of differentiation ranging from so-called cancer stem cells to differentiated cancer cells as a result of induced differentiation.

Study on Malignant Phenotype of Induced Cancer Stem Cell

Next, these cells were studied for the presence or absence of their characters as cancer cells. The induced cancer stem cells or MCF-10A cells were cultured at a density of 500 cells per 10-cm dish for 10 days. As a result, only the cancer stem cells (CSC-10A) formed a large number of cell masses (foci) (FIG. 3a). Next, these cells were subjected to metastasis/invasion assay using Matrigel-coated Transwell. The resulting images showed that only the cancer stem cells destroyed and invaded Matrigel (FIG. 3b). The cells were also cultured in soft agar. As a result, only the cancer stem cells formed a plurality of colonies (FIG. 3c). These results demonstrated that the prepared cancer stem cells had acquired malignant phenotypes (canceration) (the cells had properties as cancer cells).

Figure 4A:
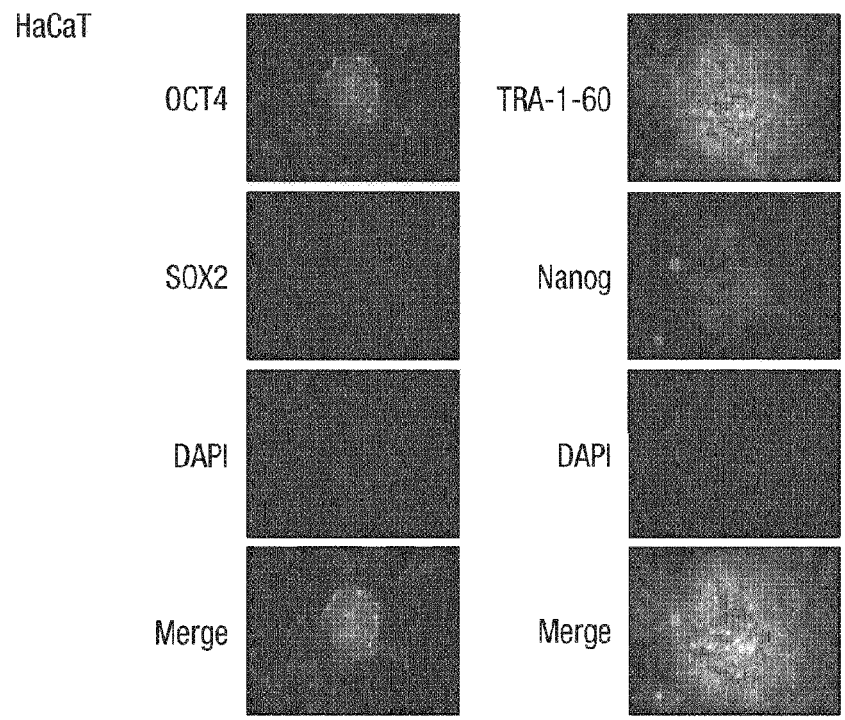
FIG. 4a shows that four reprogramming factors were expressed using the same method as used in immortalized human mammary epithelial cells to establish cancer stem cells from immortalized human skin keratinocytes HaCaT. The established colonies were immunostained with undifferentiation markers.
Figure 4B:
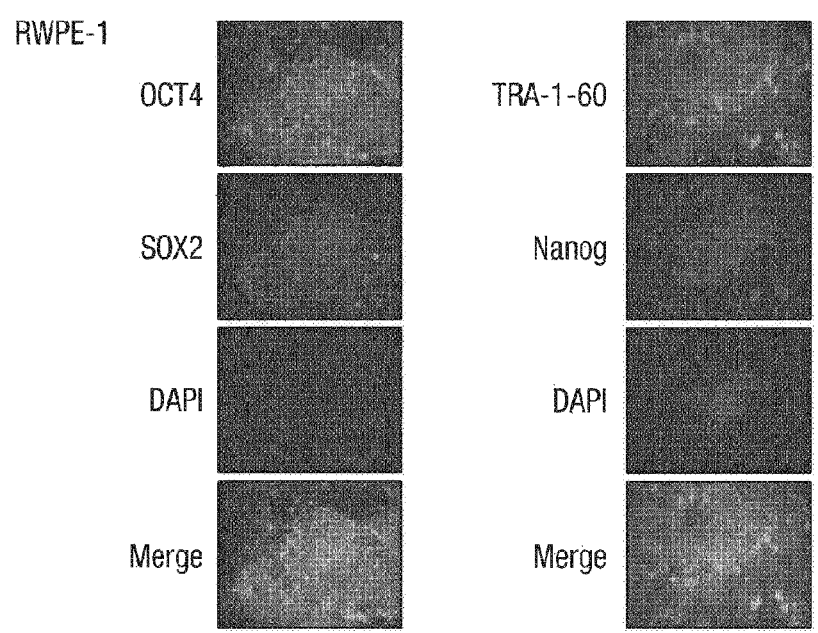
FIG. 4b shows that four reprogramming factors were expressed using the same method as used in immortalized human mammary epithelial cells to establish cancer stem cells from immortalized human prostatic epithelial cells RWPE-1. The established colonies were immunostained with undifferentiation markers.
Figure 5:
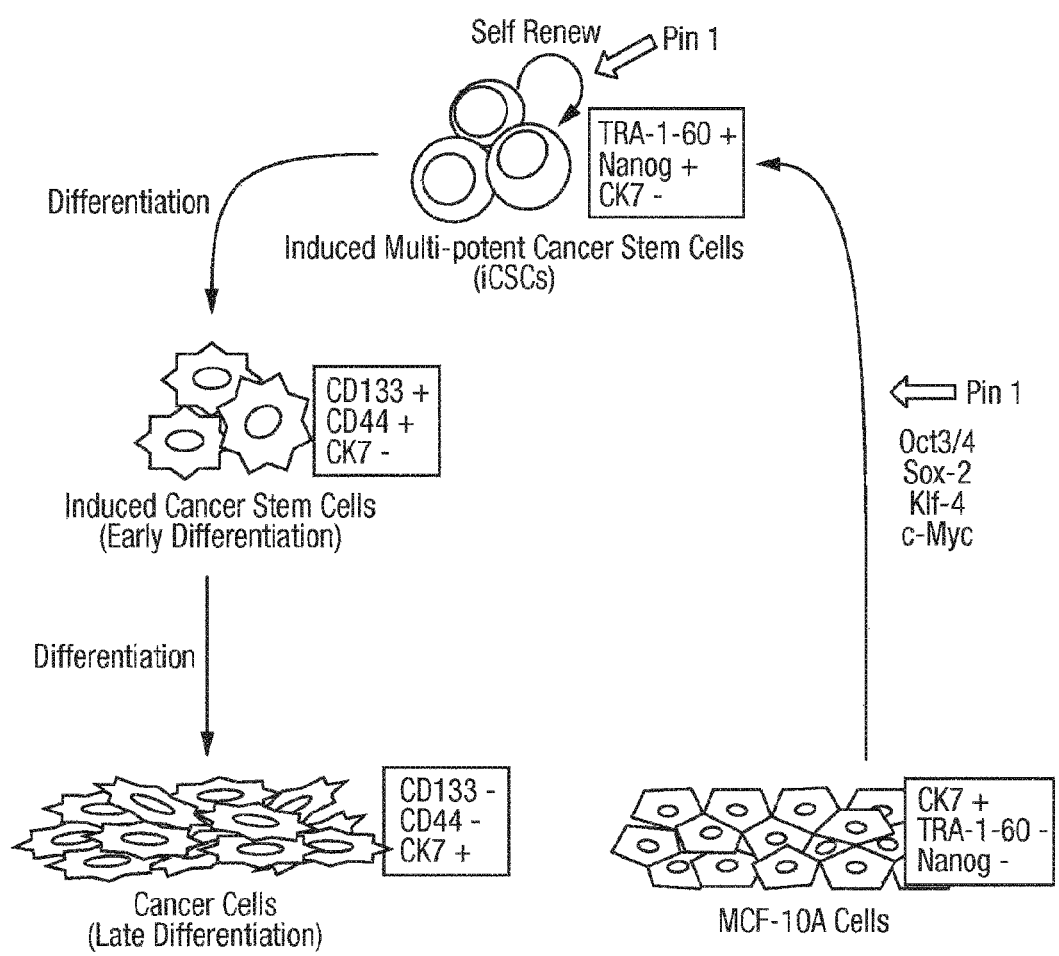
FIG. 5 is a schematic diagram showing an outline of the present invention. Cancer stem cells can be induced by the gene transfer of four reprogramming factors Oct3/4, Sox2, Klf4, and c-Myc to immortalized human epithelial cells. The additional introduction of Pin1 can promote the formation of the cancer stem cells. The induced pluripotent cancer stem cells can be further induced for differentiation into so-called cancer stem cells (CD44+, CD133+, and ABCG2+), which can be further differentiated into cancer cells that are positive to differentiated epithelial cell markers (cytokeratin (CK)7+ and CK8/18+).

Induction of Cancer Stem Cell from Immortalized Human Prostatic Epithelial Cell and Immortalized Human Skin Keratinocyte Cancer stem cells were induced by the approach of the present invention using prostatic epithelial cells RWPE-1 (Bello D, Webber M M, Kleinman H K, Wartinger D D, Rhim J S. Androgen responsive adult human prostatic epithelial cell lines immortalized by human papillomavirus 18. Carcinogenesis. 1997 June; 18 (6): 1215-23. (Establishment of RWPE-1 cells)) and skin keratinocytes HaCaT (Boukamp P, Dzarlieva-Petrusevska R T, Breitkreuz D, Hornung J, Markham A, Fusenig N E. Normal keratinization in a spontaneously immortalized aneuploid human keratinocyte cell line. J. Cell Biol. 106: 761-771, 1988. (Establishment of HaCaT cells)). As a result, a plurality of colonies expressing various pluripotent stem cell markers were successfully obtained in immunostaining, as in the case of MCF-10A cells (FIGS. 4a and 4b). These cells were thus confirmed to have properties similar to those of the MCF-10A-derived cancer stem cells described above. This means that human cancer stem cells can also be constructed from immortalized human cells by the approach of the present invention (outlined in FIG. 5).

Induced Differentiation of CSC-10A (Effects Brought about by Addition of Salinomycin)

Upon salinomycin treatment, CSC-10A differentiated and the size of each individual cell increased (upper images in FIG. 6a) whereas the staining performance of an undifferentiation marker alkaline phosphatase (lower images in FIG. 6a) decreased. The salinomycin (SMC)-treated CSC-10A cells exhibited a decrease in the expression of a stem cell (mesenchymal) marker vimentin and an increase in the expression of a differentiation (epithelial) marker beta-catenin (FIG. 6b).

<Experimental Procedures>

Cell Culture iPS cells were obtained from Riken BioResource Center (Clone No. 201B7). The iPS cells were cultured in a human ES cell culture medium (Knockout Dulbecco's modified Eagle's medium (Invitrogen Corp.) supplemented with 20% Knockout SR (Invitrogen Corp.), 1% GlutaMAX (Invitrogen Corp.), 100 mM non-essential amino acids (Invitrogen Corp.), 50 mM b-mercaptoethanol, and 10 ng/ml basic FGF) {Takahashi, Cell, 131, 861-72, 2007}.

Establishment of iCSC Cell iPS cells were prepared from MCF-10A (purchased from ATCC) using the method described in Takahashi et al. {Takahashi, Cell, 131, 861-72, 2007}. First, retrovirus vectors respectively incorporating Yamanaka's four factors (pMXs-hOct3/4, pMXs-hSox2, pMXs-hKlf4, and pMXs-hc-Myc (Addgene)) were transferred, together with VSV-G gene, to retrovirus packaging cells PLAT-E using Effectene transfection reagent (Qiagen N.V.; www.qiagen.com/products/transfection/transfectionreagents/effectenetransfectionreagent.aspx). After 48 hours, virus-containing cell supernatants were recovered, then filtered through a 0.45-um filter, and supplemented with 10 μg/ml of hexadimethrine bromide (Polybrene) to prepare a virus solution. The target cells MCF-10A were seeded at a density of $6 \times 10^5$ cells per 100-mm dish and incubated at 37° C. for 16 hours after addition of the virus solution. Then, the medium was replaced with a growth medium for mammary epithelial cells (Sanko Junyaku Co., Ltd.; www.sanko-junyaku.co.jp/product/bio/catalog/nhc/hmec.html), and the culture was continued. Six days after the viral infection, the cells were seeded over mouse fibroblasts (MEFs; feeder cells). After 24 hours, the medium was replaced with a human ES culture medium. The cells were cultured at 37° C. in a 5% $CO_2$ atmosphere for 21 days. As a result, a plurality of iPS cell-like colonies emerged.

Pickup of Cancer Stem Cells

The thus emerging plurality of iPS cell-like colonies were stained under axenic conditions using a preliminarily filter-sterilized alkaline phosphatase staining reagent (Alkaline Phosphatase Substrate Kit (VECTOR, USA)). The ES cell-like colonies stained dark-red were picked up one by one using a capillary under a microscope. The picked-up cells were cultured on feeder cells in 24-well plates and then prepared into cell clones.

Antibody

Immunostaining: anti-TRA-1-60 antibody (1:200, 14-8863, eBioscience, Inc.), anti-Nanog antibody (1:200, RCAB0003P, COSMO BIO Co., Ltd.), anti-Oct4 antibody (1:300, SC-5279, Santa Cruz Biotechnology, Inc.), anti-CD44 antibody (1:100, #3570, Cell Signaling Technology, Inc.), anti-CD133 antibody (1:50, ab16518-100, Abcam PLC), anti-ABCG2 antibody (1:100, #332002, BioLegend, Inc.), anti-CK7 antibody (1:100, M7018, DAKO), anti-CK8/18 antibody or anti-Sox2 antibody (1:2000, AB5603, Millipore Corp.), Alexa Fluor 488 goat anti-mouse IgG(H+L) (1:5000, A11001, Invitrogen Corp.), and Alexa Fluor 568 goat anti-rabbit IgG(H+L) (1:5000, A11011, Invitrogen corp.)

Western blot: anti-actin antibody (1:5000, A5316, Sigma-Aldrich Inc.) and anti-Klf4 antibody (1:2000, SC-20691, Santa Cruz Biotechnology, Inc.)

FACS: anti-CD24 antibody (1:50, 555574, BC Pharmingen) and anti-CD44 antibody (1:50, 555478, BC Pharmingen) RT-PCR RNAs purified from cells were treated with reverse transcriptase ReverTraAce-a (Toyobo, Japan) to prepare cDNAs. PCR was performed using Ex-Taq (Takara, Japan).

```
PCR primer
Sox2: Fw;
                                       (SEQ ID NO: 3)
GGGAAATGGGAGGGGTGCAAAAGAGG, Rv;
                                       (SEQ ID NO: 4)
TTGCGTGAGTGTGGATGGGATTGGTG Oct4: Fw;
                                       (SEQ ID NO: 5)
GACAGGGGGAGGGGAGGAGCTAGG, Rv;
                                       (SEQ ID NO: 6)
CTTCCCTCCAACCAGTTGCCCCAAAC Nanog: Fw;
                                       (SEQ ID NO: 7)
CAGCCCtGATTCTTCCACCAGTCCC, Rv;
                                       (SEQ ID NO: 8)
tGGAAGgTTCCCAGTCGGGTTCACC DNMT3: Fw;
                                       (SEQ ID NO: 9)
TGCTGCTCACAGGGCCCGATACTTC, Rv;
                                       (SEQ ID NO: 10)
TCCTTTCGAGCTCAGTGCACCACAAAAC UTF1: Fw;
                                       (SEQ ID NO: 11)
CCGTCGCTGAACACCGCCCTGCTG, Rv;
                                       (SEQ ID NO: 12)
CGCGCTGCCCAGAATGAAGCCCAC GAPDH: Fw;
                                       (SEQ ID NO: 13)
GTGGACCTGACCTGCCGTCT, Rv;
                                       (SEQ ID NO: 14)
GGAGGAGTGGGTGTCGCTGT
```

Karyotype Analysis

The analysis was consigned to Nihon Gene Research Laboratories Inc. (www.ngrl.co.jp/). Karyotype analysis was conducted to know various factors including the number of chromosomal copies, the presence or absence of translocation or deletion, etc. As a result of the karyotype analysis, the present cells had chromosomal states substantially identical to those of the parental MCF-10A cells and hence are highly likely to be cancer stem cells induced via epigenetic changes. These cells may potentially be applicable in various screening fields as cancer stem cell models having a minimum accumulation of gene mutations.

Tumor Formation Using Immunodeficient Mouse

The cells were dissociated using Accutase, then recovered into tubes, and centrifuged. The precipitated cells were suspended in a human ES culture medium. $2 \times 10^6$ cells were mixed with an equal amount of Matrigel (354234, BD Biosciences) and subcutaneously injected into each NOD-SCID mouse (CREA, Tokyo, Japan). After 9 weeks, tumors were excised. Frozen tumor tissues were embedded in an optimum cutting temperature compound (OCT). Then, frozen sections were prepared and stained with hematoxylin and eosin.

In Vitro Induced Differentiation Method

The iCSC cells were detached into single cells using Accutase and then seeded at a density of 10000 cells per 96 wells over ultra low attachment culture plates. The medium used was Knockout Dulbecco's modified Eagle's medium (Invitrogen Corp.) supplemented with 20% FBS, 1% GlutaMAX (Invitrogen Corp.), 100 mM non-essential amino acids (Invitrogen Corp.), and 50 mM b-mercaptoethanol. Seven days after the start of suspension culture, EB-like cells were transferred to gelatin-coated dishes and further cultured in the same medium as above for 9 days, followed by culture in DMEM.

FACS Analysis

The CSC-10A cells were detached using 0.02% EDTA and suspended in an FACS buffer (3% FBS/0.1% $N_aN3$/PBS). After centrifugation at 3000 rpm at room temperature for 5 minutes, the cells were suspended again in an FACS buffer, then centrifuged, and washed. The cells were suspended at a concentration of $2 \times 10^5$ cells/ml in an FACS buffer and dispensed into Eppendorf tubes in 50-ul portions. Ten microliters each of PE-labeled anti-CD24 and FITC-labeled anti-CD44 antibodies were added into the tubes which were subsequently left in ice for 30 minutes. One milliliter of an FACS buffer was added to the cells, which were then centrifuged. The cells were suspended again in an FACS buffer, then centrifuged, washed, and suspended in 100 ul of an FACS buffer. The cells were fixed in ice for 15 minutes with 100 ul of added 4% paraformaldehyde. The stained cells were assayed using an FACS apparatus.

Focus Formation Assay

The cells were detached using a trypsin/EDTA mixed solution and suspended in a cell growth medium for usual culture. The cells were seeded at a density of 500 cells per 10 cm dish and cultured for 10 days. After 10 days, the cells were stained with a crystal violet reagent and then destained with 70% ethanol. Subsequently, the number of foci was determined.

Colony Formation Assay

A sample of 0.5% soft agar containing 10% FBS was dispensed into dishes and left at room temperature for 15 minutes. When the soft agar solidified, it was overlayered with a mixed solution of 0.33% soft agar and 1000 cells and culture was performed for 10 days. After 10 days, the number of colonies was counted using a phase-contrast microscope.

Invasion Assay

Matrigel was diluted with serum-free DMEM to give a concentration of 1 mg/ml and dispensed into 24-well Transwell at 100 ul/well. The Transwell was left at 37° C. for 5 hours until the Matrigel solidified. The cells were detached using trypsin, then washed three times with DMEM containing 1% FBS, and suspended in 1% FBS containing DMEM at a concentration of $1\times10^6$ cells/ml. The Transwell was mildly washed with serum-free DMEM. The cells were seeded on the Transwell. The lower plate was filled with 600 ul of 10% DMEM containing 5 ug/ml of fibronectin. After incubation at 37° C. for 24 hours, the wells were washed with PBS. The cells were fixed by adding 3% formalin. The cells in the Transwell were stained with a crystal violet staining solution for 5 minutes. Then, uninvaded cells on the upper surface of the Transwell were swabbed away.

Induced Differentiation Method for CSC-10A (Addition of Salinomycin)

CSC-10A was seeded over 10-cm dishes. After 24 hours, salinomycin was added to give a final concentration of 10 and the culture was continued at 37° C. Four days after the addition of salinomycin, the cells were stained with alkaline phosphatase. The cells were recovered four days after the addition of salinomycin and subjected to Western blot which confirmed the expression of vimentin, β-catenin, and tubulin (control).

All publications, patents, and patent applications cited herein are incorporated herein by reference in their entirety.

INDUSTRIAL APPLICABILITY

By making effective use of the cancer stem cell model of the present invention, proteins that are specifically expressed in cancer stem cells or their posttranslational modifications can be identified using a suitable approach such as proteomics or microarrays so as to elucidate their functions or roles in the formation or maintenance (self-renewal ability and pluripotency) of the cancer stem cells. In addition, cancer stem cell-specific monoclonal antibodies can be prepared by transplanting the cell line of the present invention into mice, rats, or the like. As a result, factors or targets that inhibit the formation of cancer stem cells can be identified. In addition, the biological characteristics of cancer stem cells and their similarity to or difference from normal stem cells can be elucidated, thereby leading to the development of novel therapeutic methods targeting cancer stem cells. Furthermore, factors that induce the differentiation of cancer stem cells at each stage of differentiation can be screened for to identify factors that inhibit the maintenance of self-renewal or pluripotency of cancer stem cells. The identified factors can contribute to the development of novel methods for treating cancer stem cells.

Free Text for Sequence Listing

```
<SEQ ID NO: 1>
SEQ ID NO: 1 represents the cDNA sequence (492 bp; stop
codon is underlined) of human Pin1.
atggcgga cgaggagaag ctgccgcccg gctgggagaagcgcatgagc cgcagctcag
gccgagtgta ctacttcaac cacatcacta acgccagccagtgggagcgg
cccagcggca acagcagcag tggtggcaaa aacgggcagg gggagcctgc
cagggtccgc tgctcgcacc tgctggtgaa gcacagccag tcacggcggc
cctcgtcctg gcggcaggag aagatcaccc ggaccaagga ggaggccctg
gagctgatca acggctacat ccagaagatc aagtcgggag aggaggactt
tgagtctctg gcctcacagt tcagcgactg cagctcagcc aaggccaggg
gagacctggg tgccttcagc agaggtcaga tgcagaagcc atttgaagac
gcctcgtttg cgctgcggac gggggagatg agcgggcccg tgttcacgga
ttccggcatc cacatcatcc tccgcactga gtag <SEQ ID NO: 2>
SEQ ID NO: 2 represents the amino acid sequence (163
amino acids) of human Pin1.
madeeklppg wekrmsrssg rvyyfnhitn asqwerpsgn sssggkngqg
eparvrcshllvkhsqsrrp sswrqekitr tkeealelin gyiqkiksge
edfeslasqf sdcssakargdlgafsrgqm qkpfedasfa lrtgemsgpv
ftdsgihiil rte <SEQ ID NO: 3>
SEQ ID NO: 3 represents the sequence of a PCR primer (Fw)
for Sox2.
GGGAAATGGGAGGGGTGCAAAAGAGG <SEQ ID NO: 4>
SEQ ID NO: 4 represents the sequence of a PCR primer (Rv)
for Sox2.
TTGCGTGAGTGTGGATGGGATTGGTG <SEQ ID NO: 5>
SEQ ID NO: 5 represents the sequence of a PCR primer (Fw)
for Oct4.
GACAGGGGGAGGGGAGGAGCTAGG <SEQ ID NO: 6>
SEQ ID NO: 6 represents the sequence of a PCR primer (Rv)
for Oct4.
CTTCCCTCCAACCAGTTGCCCCAAAC <SEQ ID NO: 7>
SEQ ID NO: 7 represents the sequence of a PCR primer (Fw)
for Nanog.
CAGCCCtGATTCTTCCACCAGTCCC
```

Free Text for Sequence Listing

<SEQ ID NO: 8>
SEQ ID NO: 8 represents the sequence of a PCR primer (Rv) for Nanog.
tGGAAGgTTCCCAGTCGGGTTCACC <SEQ ID NO: 9>
SEQ ID NO: 9 represents the sequence of a PCR primer (Fw) for DNMT3.
TGCTGCTCACAGGGCCCGATACTTC <SEQ ID NO: 10>
SEQ ID NO: 10 represents the sequence of a PCR prime r(Rv) for DNMT3.
TCCTTTCGAGCTCAGTGCACCACAAAAC <SEQ ID NO: 11>
SEQ ID NO: 11 represents the sequence of a PCR primer (Fw) for UTF1.
CCGTCGCTGAACACCGCCCTGCTG <SEQ ID NO: 12>
SEQ ID NO: 12 represents the sequence of a PCR primer (Rv) for UTF1
CGCGCTGCCCAGAATGAAGCCCAC <SEQ ID NO: 13>
SEQ ID NO: 13 represents the sequence of a PCR primer (Fw) for GAPDH.
GTGGACCTGACCTGCCGTCT <SEQ ID NO: 14>
SEQ ID NO: 14 represents the sequence of a PCR primer (Rv) for GAPDH.
GGAGGAGTGGGTGTCGCTGT

The invention claimed is:

1. A method for preparing human cancer stem cells expressing CD44(+)/CD24(−/low), CD133 and ABCG2 in vitro, comprising:
   obtaining immortalized epithelial cells selected from the group consisting of human mammary epithelial cell MCF-10A, human prostatic epithelial cell RWPE-1, and human skin keratinocyte HaCaT;
   transducing the immortalized epithelial cells with a recombinant retroviral or sendai virus vector Oct3/4, Sox2, Klf4, and c-Myc genes;
   culturing the transduced immortalized epithelial cells for a sufficient time in a mammary epithelial cell growth medium for to reprogram the cells;
   seeding the transduced cells on feeder cells in the presence of in a human embryonic stem cell medium containing bFGF for a sufficient period of time to form colonies expressing alkaline phosphatase;
   staining the transduced cell colonies with alkaline phosphatase to obtain a number of alkaline phosphatase staining-positive cell colonies;
   selecting an alkaline phosphatase staining-positive cell colony among colonies formed with the cells transduced with Oct3/4, Sox2, Klf4, and c-Myc genes to obtain homogenous pluripotent cancer stem cells expressing pluripotent cancer stem cell markers TRA-1-60 and NANOG, but not expressing CK7;
   culturing the pluripotent cancer stem cells in suspension to form an embryoid body; and
   culturing the embryoid body on an adhesion substrate thereby obtaining human cancer stem cells expressing CD44(+)/CD24(−/low), CD133 and ABCG2.

2. The method of claim 1, further comprising culturing the human cancer stem cells for a sufficient period of time to obtain cancer cells expressing a differentiation epithelial cell marker selected from CK7 or CK8/18.

3. The method of claim 1, wherein said adhesion substrate comprises a plate.

4. The method of claim 3, wherein said plates are uncoated.

5. The method of claim 1, wherein said substrate comprises a dish and the embryoid bodies are cultured in said dish until the cells of the embryoid body adhere as a single layer to the bottom of the dish.

6. The method of claim 1, wherein the immortalized epithelial cell is human mammary epithelial cell MCF-10A.

7. The method of claim 1, wherein the immortalized epithelial cell is human prostatic epithelial cell RWPE-1.

8. The method of claim 1, wherein culturing the pluripotent cancer stem cell in suspension occurs for 7 days.

9. The method of claim 8, wherein culturing the embryoid body on the adhesion substrate occurs for 2 days.

* * * * *